United States Patent
Hobson et al.

(10) Patent No.: US 7,307,191 B2
(45) Date of Patent: Dec. 11, 2007

(54) ORGANIC PEROXYACID PRECURSORS

(75) Inventors: David W. Hobson, San Antonio, TX (US); Danny O. Helton, Newberry, FL (US)

(73) Assignee: OH Technologies LLP, Boerne, TX (US)

( * ) Notice: Subject to any disclaimer, the term of this patent is extended or adjusted under 35 U.S.C. 154(b) by 270 days.

(21) Appl. No.: 10/800,788

(22) Filed: Mar. 16, 2004

(65) Prior Publication Data

US 2004/0176267 A1   Sep. 9, 2004

Related U.S. Application Data

(63) Continuation-in-part of application No. 10/752,430, filed on Jan. 6, 2004, now Pat. No. 7,005,549.

(60) Provisional application No. 60/438,114, filed on Jan. 6, 2003.

(51) Int. Cl.
*C07C 311/00* (2006.01)

(52) U.S. Cl. .................. 568/30; 564/154; 564/192; 568/31; 252/186.38; 510/376

(58) Field of Classification Search .............. None
See application file for complete search history.

(56) References Cited

U.S. PATENT DOCUMENTS

| | | | |
|---|---|---|---|
| 3,267,139 A * | 8/1966 | Lafferty | 564/79 |
| 3,956,396 A | 5/1976 | Mageli et al. | 260/610 |
| 4,151,106 A | 4/1979 | Meenen | 252/186 |
| 4,255,277 A | 3/1981 | Smearing | 252/186 |
| 4,396,527 A | 8/1983 | Matsuyama et al. | 252/186.23 |
| 4,401,663 A | 8/1983 | Buckwalter et al. | 424/321 |
| 4,842,765 A | 6/1989 | Satomi | 252/186.26 |
| 4,917,816 A | 4/1990 | Self | 252/186.26 |
| 5,057,479 A | 10/1991 | Bock | 502/160 |
| 5,110,495 A | 5/1992 | Self | 252/186.26 |
| 5,162,280 A | 11/1992 | Bock | 502/160 |
| 5,596,017 A * | 1/1997 | Otsu et al. | 514/517 |
| 5,654,464 A | 8/1997 | Abma et al. | 558/261 |
| 5,773,459 A | 6/1998 | Tang et al. | 514/445 |
| 6,174,922 B1 | 1/2001 | Arnold et al. | 514/604 |
| 6,303,816 B1 | 10/2001 | Arnold et al. | 564/82 |
| 6,500,865 B1 | 12/2002 | Arnold et al. | 514/605 |

FOREIGN PATENT DOCUMENTS

DE   1801713   *   6/1970
DE   1953920   *   5/1971

OTHER PUBLICATIONS

DE 1953920; May 6, 1971; translation.*
DE 1801713; Jun. 11, 1970; translation.*

* cited by examiner

*Primary Examiner*—Gregory R. Del Cotto
(74) *Attorney, Agent, or Firm*—Christopher J. Whewell

(57) ABSTRACT

This present invention provides materials for use as solid or concentrated chemical precursors for the production of organic peroxy acids (peracids). Organic peroxy acids are formed using a precursor according to the invention when they are combined with hydrogen peroxide or a hydrogen peroxide precursor such as a percarbonate or a perborate in aqueous medium. Organic peroxy acids, such as peroxyacetic acid, are used currently to disinfect medical equipment such as endoscopes and related items.

7 Claims, No Drawings

ORGANIC PEROXYACID PRECURSORS

CROSS-REFERENCES TO RELATED APPLICATIONS

This application is a Continuation-In-Part of U.S. patent application Ser. No. 10/752,430 filed on Jan. 6, 2004 now U.S. Pat. No. 7,005,549, and claims the benefit of U.S. Provisional Application No. 60/438,114 filed Jan. 6, 2003 the entire contents of both of which are herein incorporated by reference.

TECHNICAL FIELD

This invention relates generally to organic peroxy acids and more particularly to chemical precursors from which peroxygen acids (peroxy acetic, peroxy propionic, etc.) may be advantageously prepared upon mixing the inventive precursors with hydrogen peroxide or a peroxide precursor, such as percarbonate or perborate anions, in aqueous media. The inventive compounds are conveniently prepared from reacting an alkyl, aryl, or alkylaryl acyl halide with various substituted or unsubstituted sulfamides and sulfoxamides.

BACKGROUND

Various workers in the prior art have provided compositions and methods for generating sterilization and disinfecting compositions, a few of which include those in the following US patents, which are herein incorporated by reference thereto. U.S. Pat. No. 2,454,254 teaches a stabilized organic peroxide composition which contains a single phase liquid mixture of an alkyl ester of phthalic acid and an organic peroxide. U.S. Pat. No. 3,520,825 provides an organic peroxide containing paste containing from 20-65% of a solid peroxide, water, and a polyethylene glycol having a molecular weight of at least about 1000. U.S. Pat. No. 3,956,396 teaches a safe diacyl peroxide solution composition consisting essentially of: a diacyl peroxide at about 10-70% by weight; and a safety solvent for the peroxide, at about 90-30% by weight. The solvent is present in such an amount to render the solution composition safe, where the solvent is selected from the group consisting of aliphatic hydrocarbons, aliphatic ketones, aliphatic esters, aliphatic ethers, aliphatic alcohols and mixtures thereof, which boils in the range of about 140-210° C. at 760 mm. Hg, and has a vapor pressure substantially the same as that of the peroxide. U.S. Pat. No. 4,151,106 provides a process for the preparation of uniform, stable diacyl peroxide compositions comprising reacting the corresponding acyl chloride with hydrogen peroxide in an alkaline aqueous medium in the presence of a desensitizing agent. U.S. Pat. No. 4,255,277 describes a storage stable peroxide paste composition comprising: benzoyl peroxide or benzoyl peroxide having one or more substituents selected from halogen, lower alkyl or lower alkoxy; and a minor proportion of water; and finely divided particulate calcium carbonate in an amount sufficient to prevent the composition from physically separating into its components. U.S. Pat. No. 4,396,527 sets forth an aqueous emulsion of organic peroxide which is obtained by incorporating a water soluble alcohol of low molecular weight into a system which comprises an organic peroxide, an emulsifier and water. U.S. Pat. No. 4,917,816 provides an organic peroxide aqueous dispersion comprising: a) from about 35 to about 70 weight percent of solid benzoyl peroxide particles, the particles having a size of about 10 microns or less; b) water; c) a compound that produces an ionic region about the peroxide particles in the dispersion, is inert as to the peroxide, and is at least water dispersible wherein the compound is selected from the group consisting of finely divided filmed silica, a sodium salt of a condensed naphthalene sulfonic acid and a sodium salt of a polymerized carboxylic acid; d) a defoamer; and e) a water soluble acidic inorganic salt which is inert as to the peroxide and which increases the viscosity of the dispersion, retains water of hydration upon dry down of the dispersion and possesses fire retardant properties. U.S. Pat. No. 5,057,479 discloses an aqueous dispersion for use in curing polyester resins and the suspension polymerization of vinyl monomers comprising a symmetrical or asymmetrical aromatic diacyl peroxide; a water-soluble alkylene glycol; a dispersion stabilizing amount of magnesium aluminum silicate and a cellulose ether; and sufficient water to form an aqueous dispersion. U.S. Pat. No. 5,110,495 teaches an improved organic peroxide dispersion comprising: a) from about 35 to about 70 weight percent of solid organic peroxide having a particle size of 10 microns or less; b) from about 65 to 30 weight percent water; c) a dispersant, the dispersant being inert as to the peroxide and at least water dispersible and producing a dispersion having a predetermined Brookfield viscosity of at least 100 centipoises; and d) a defoamer. U.S. Pat. No. 5,654,464 teaches organic peroxide compositions which contain a cyclic alpha-diketone compound to retard the rate of decomposition of the peroxide compound.

Peroxyacids, and peroxyacetic acid in particular, have been used with considerable success in cleaning and disinfecting various surfaces and implements, including medical devices such as endoscopes, and some other environmental surfaces. However, one drawback associated with the use of peroxyacetic acid and other peroxy acids in such an end use at its final use concentrations of about 0.05% to about 5% by weight is too unstable to have a useful shelf life. In practical terms, the shelf life of such solutions is limited to a few months, rather than years, due to the inherent instability of the materials. Generally, very low concentrations of the peroxyacetic species, such as those used to disinfect surfaces (i.e., 0.05% to about 5%) are too unstable for a useful commercial shelf life. Thus, it has been found necessary when desiring to employ these materials to provide a concentrated solution immediately prior to its use and diluting to the final desired concentration. One way around the shelf life problem could be to employ a solid formulation which is mixed with water shortly before needed. According to such a method as used within the context of the prior art, active precursor components include a solid form of hydrogen peroxide such as an alkali or alkaline earth percarbonate or perborate salt in combination with an acyl donor, such as either tetraacetylethylenediamine ("TAED") or acetylsalicylic acid. The aqueous peroxyacid generation process is described by the reaction:

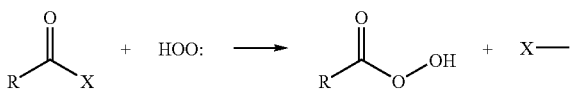

with the understanding that the peroxide is present a result of the reaction of the perborate or percarbonate with water, and is subsequently available to react with the acyl compound. In the foregoing equation, the radical X represents the remaining residue of the TAED or ASA molecule, such as in the case of ASA wherein it represents the ASA molecule minus the acetyl group. However, we do not consider TAED and ASA to be efficient acylating agents, in that a relatively large mass of useless carbon-containing byproducts are generated when these reactants are employed. In addition, the kinetics of the reaction are not as favorable as would be desired, viz., to quickly generate appreciable quantities of peroxyacetic acid from ASA according to the above scheme, a reaction temperature above room temperature is required.

While peroxyacetic acid is currently used to disinfect medical equipment such as endoscopes and related items, peroxypropionic acid ("PPA") has not been developed for such purposes due at least in part to the lack of an efficient means to produce PPA at the site of use.

The precursors of the present invention have the distinct advantage that they can be used to produce novel antimicrobial formulations which contain PPA, as well as a whole host of other peroxyacids which are relatively easy to produce and which consume less weight of hydrogen peroxide during their production per mole of peroxyacid produced than the commercial precursors acetyl salicylic acid (ASA) and tetraacetylethylenediamine (TAED), which is a great advantage. Additionally, the precursors of the present invention allow for the formulation of antimicrobial compositions that have room temperature stability in their concentrated forms and can alternatively be packaged in dry powder form for reconstitution by combination with hydrogen peroxide, or a hydrogen peroxide precursor/water mixture at the site of their end use. Thus, the resulting liquid formulations can be readily delivered in liquid or even gaseous form at the site of use. The dry powder form or its concentrate may also be applied to the site of use and activated with hydrogen peroxide or water in combination with a hydrogen peroxide precursor.

Thus, in summary, the present invention provides novel water-soluble precursors useful for generating peroxy acids more efficiently than previously provided for by the prior art. When using a precursor of the present invention, there are less by-products generated for every mole of peroxyacid generated. Further, a smaller weight of the precursor provided by the present invention is required to generate a mole of peroxy acid than when using prior art materials and/or methods. The acyl precursors provided by the present invention are generally more water-soluble than ASA, relatively inexpensive to manufacture, and consume less weight of acyl precursor per mole of peroxyacid generated than the corresponding ASA. Immediate uses for the solutions provided by the use of the various embodiments of this invention include, without limitation: emergency disinfection of wounds by mixing dry powder with water; disinfection of surgical facilities and medical treatment rooms; chemical sterilization of surgical equipment and instruments, particularly endoscopes; disinfection of medical devices; disinfection of animal enclosure areas such as used by horses, cattle, dogs, cats, etc.; remediation of mold in buildings, the contents of buildings; disinfecting plants and foodstuffs, including meats, vegetables, and fruits; disinfection of surfaces from vegetative bacteria, molds, fungi and their spores, especially for remediation in non-line-of-slight applications; and liquid disinfectants of equipment such as tanks, passenger cars, all military vehicles, aircraft, and related equipment.

SUMMARY OF THE INVENTION

The present invention provides compositions of matter useful for forming peroxygen acids, which comprise an amino compound having the structure:

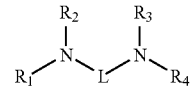

in which L is a divalent radical that is independently selected from the group consisting of:

and wherein $R_1$, $R_2$ $R_3$, and $R_4$ are each independently selected from the group consisting of: hydrogen, any $C_1$ to $C_{20}$ hydrocarbyl group, and the group:

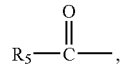

subject to the proviso that: at least one of $R_1$, $R_2$, $R_3$, and $R_4$ are the group:

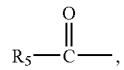

in which $R_5$ is in each occurrence independently hydrogen or any $C_1$ to $C_{20}$ hydrocarbyl group.

According to one general alternate embodiment of the invention, one and only one of $R_1$, $R_2$, $R_3$, and $R_4$ is the group:

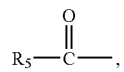

in which $R_5$ is independently hydrogen or any $C_1$ to $C_{20}$ hydrocarbyl group. One variation of this alternate embodiment is where at least one of the groups of $R_1$, $R_2$, $R_3$, and $R_4$ which are not the group:

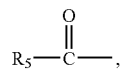

is hydrogen. Another variation of this alternate embodiment is where at least one of the groups of $R_1$, $R_2$, $R_3$, and $R_4$ which are not the group:

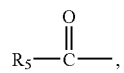

is independently in each occurrence any $C_1$ to $C_{20}$ hydrocarbyl group.

According to a second general alternate embodiment of the invention, any two of $R_1$, $R_2$, $R_3$, and $R_4$ are the group:

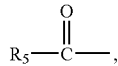

in which $R_5$ is independently in each occurrence hydrogen or any $C_1$ to $C_{20}$ hydrocarbyl group. One variation of this second general alternate embodiment is where at least one of the groups of $R_1$, $R_2$, $R_3$, and $R_4$ which are not a group:

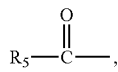

is hydrogen. Another variation of this second general alternate embodiment is where at least one of the groups of $R_1$, $R_2$, $R_3$, and $R_4$ which are not a group:

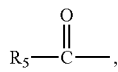

is independently in each occurrence any $C_1$ to $C_{20}$ hydrocarbyl group.

According to a third general alternate embodiment of the invention any three of $R_1$, $R_2$, $R_3$, and $R_4$ are the group:

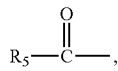

in which $R_5$ is independently in each occurrence hydrogen or any $C_1$ to $C_{20}$ hydrocarbyl group, and the group of $R_1$, $R_2$, $R_3$, and $R_4$ which is not a group:

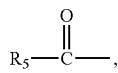

is hydrogen. One variation of this third general alternate embodiment is where the group of $R_1$, $R_2$, $R_3$, and $R_4$ which is not a group:

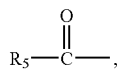

is any $C_1$ to $C_{20}$ hydrocarbyl group. Another variation of this third general alternate embodiment is where all of $R_1$, $R_2$, $R_3$, and $R_4$ are the group:

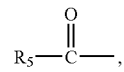

in which $R_5$ is independently in each occurrence hydrogen or any $C_1$ to $C_{20}$ hydrocarbyl group.

A fourth general alternate embodiment of the invention is where $R_1$ and $R_4$ are represented by the group:

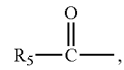

in which $R_5$ is independently in each occurrence hydrogen or any $C_1$ to $C_{20}$ hydrocarbyl group, and wherein $R_2$ and $R_3$ are each independently selected from the group consisting of: hydrogen, and any $C_1$ to $C_{20}$ hydrocarbyl group. A variation of this fourth general embodiment is where $R_5$ in each occurrence is selected from the group consisting of: methyl, ethyl, 1-propyl, and 2-propyl.

The aforesaid amino compounds generally exist in the form of solids at room temperature, and it is a routine matter to dry them to form a dry powder. Thus, is a simple matter to mix an amino compound of the invention with any number of known solid compounds which upon being contacted with water yield a peroxide, such as hydrogen peroxide and peroxide ions. Examples of such materials include alkali and alkaline earth metal salts of percarbonates and perborates. According to such an embodiment comprising a dry powder which includes an amino compound and a source of peroxide, it is desired that the amino compound is present between about 0.1% and about 5% by weight based on the total weight of said composition.

The invention also provides a process for providing an aqueous peroxy acid comprising contacting a composition containing an amino compound of the invention with an aqueous peroxide, such as hydrogen peroxide or any other source of peroxide ions. Thus, the invention provides aqueous solutions containing an amino compound of the invention. Typically, an aqueous solution of the invention contains water present in any amount between about 80% and about 99.95% by weight based on the total weight of the aqueous solution, and the inventive amino compounds may be present in any amount between about 0.1% and about 5% by weight based upon the total weight of such an aqueous solution. Various additives may be included in such aqueous solutions, including buffers, surfactants, sequesterants, etc.

The invention also provides compositions which comprise an aqueous solution of the amino compounds of the invention which further comprise at least one solid compound which upon being contacted with water yields a peroxide such as hydrogen peroxide or peroxide ions. Typical examples of suitable solid compounds include alkali and alkaline earth metal salts of percarbonates and perborates. One embodiment provides for the peroxide-generating compound to be present in any amount between about 0.01% and about 5% by weight based upon the total weight of the aqueous solution.

The invention also provides methods for disinfecting surfaces by contacting any surface with a mixture comprising: water, any of the various amino compounds provided herein, and a source of peroxide, such as hydrogen peroxide or peroxide ions.

The invention also provides methods for volatilizing a peroxy acid by mixing water, any of the various amino compounds provided herein, and a source of peroxide, such as hydrogen peroxide or peroxide ions under conditions sufficient to enable evolution of a peroxy acid in aqueous solution. Generally, for this to occur, all which needs to happen is that a peroxy acid be formed in aqueous solution by mixing the above-specified components. For peroxy acids that don't rapidly form vapors, conventional vaporization methods such as sonication, heating, and venturi effect may be used.

DETAILED DESCRIPTION

One embodiment of the present invention provides chemical precursors from which organic peroxy acids may be prepared upon their being mixed with hydrogen peroxide or another suitable peroxide precursor, such as percarbonate or perborate anions or species, in aqueous media. The inventive compounds include those described by the chemical formula:

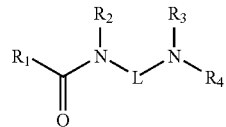

in which L is a divalent radical that is independently selected from the group consisting of:

and wherein $R_1$ is independently any $C_1$ to $C_{20}$ hydrocarbyl group; $R_2$ is independently selected from the group consisting of: hydrogen, any $C_1$ to $C_{20}$ hydrocarbyl group, and the group:

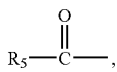

in which $R_5$ is independently hydrogen or any $C_1$ to $C_{20}$ hydrocarbyl group;

$R_3$ is independently selected from the group consisting of: hydrogen and any $C_1$ to $C_{20}$ hydrocarbyl group; and $R_4$ is independently selected from the group consisting of: hydrogen, and the group

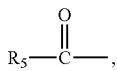

in which $R_5$ is independently hydrogen or any $C_1$ to $C_{20}$ hydrocarbyl group.

The precursors of this embodiment of the invention are conveniently prepared by reacting an acid halide of a carboxylic acid with various substituted or unsubstituted sulfamides and sulfoxamides in an appropriate solvent. An acid halide of a carboxylic acid is often referred to by those skilled in the art as simply an "acid halide". Acid halides of carboxylic acids, (including without limitation alkyl carboxylic acids, aryl carboxylic acids and alkylaryl carboxylic acids), are well known in the art, and are believed to be described in all reputable college-level organic chemistry textbooks, one example being "Introduction to Organic Chemistry", by Streitweiser and Heathcock, $2^{nd}$ ed. MacMillan Publishing Company, New York (1981), the entire contents of which are herein incorporated by reference, especially pages 517, et seq. The acid halides of carboxylic acids may be formed as the reaction product between a carboxylic acid and a suitable halogenating agent such as the trichloride and pentabromide of phosphorous, or the thionyl halides such as thionyl chloride and thionyl bromide, under conditions well known to the organic chemist. In the formation of acid halides by this route, the hydroxy group of the carboxylic acid function is replaced by a halogen atom, usually chlorine or bromine. Thus, in general, an acid halide useful for forming a precursor in accordance with the present invention has the chemical structure:

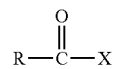

in which R is any $C_1$ to about $C_{20}$ hydrocarbyl group, and in which X is any halogen atom. This definition includes the acid halides of alkyl carboxylic acids, as well as the acid halides of aryl carboxylic acids and alkylaryl carboxylic acids. According to one preferred form of the invention, the halogen atom X comprises bromine or chlorine.

The term "hydrocarbyl", when referring to a substituent or group in the present specification and the claims appended hereto is used in its ordinary sense, which is well-known to those skilled in the art. Specifically, it means a group having a carbon atom directly attached to the remainder of the molecule and having predominantly hydrocarbon character. Examples of hydrocarbyl substituents or groups include: (1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical); (2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy); (3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group. All hydrocarbyl groups are useful within the meaning of R in the above formula for the acid halide, subject to the proviso that no portion of the hydrocarbyl radical R present is detrimentally reactive with the labile carbonyl-halogen bond also present within the time frame of the use of such acid halide in preparation of the targeted precursor.

Thus, typical acid halides suitable for use in preparing a precursor according to the present invention include, without limitation: acetyl chloride, adipoyl chloride, anisoyl chloride, acryloyl chloride, butyryl chloride, camphoroyl chloride, caproyl chloride, cinnamoyl chloride, cyanoacetyl chloride, formyl chloride, proprionyl chloride, fumaroyl chloride, glutaryl chloride, isophthaloyl chloride, levulinoyl chloride, lauroyl chloride, malonyl chloride, oleoyl chloride, oxalyl chloride, pyruvoyl chloride, salicyloyl chloride, stearoyl chloride, suberoyl chloride, terephthaloyl chloride, thioacetyl chloride, phthaloyl chloride, succinyl chloride, benzoyl chloride, maleyl chloride and toluoyl chloride. In fact, all known acid halides are in principle useful as acid halides from which a precursor according to the invention may be provided, owing to the presence of an active hydrogen atom in the molecular structure of the co-reactant with which the acid halide is reacted to form the inventive precursors.

The co-reactant used as a precursor with which an acid halide is reacted in order to form a precursor of the invention is selected from the group consisting of substituted or unsubstituted sulfamides and sulfoxamides. Sulfamide is a compound well-known to have the structure:

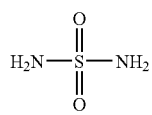

and sulfoxamide is a compound well known in the art to have the structure:

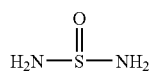

Each of these compounds comprise two nitrogen atoms, each of which have at least one active hydrogen atom attached thereto. For purposes of this invention and the appended claims, a hydrogen atom attached to a nitrogen atom of a substituted or unsubstituted sulfamide or sulfoxamide is considered to be an active hydrogen atom if it is capable of participating in the Zerevitinov reaction (Th. Zerevitinov, Ber. 40, 2023 (1907)) to liberate methane from methylmagnesium iodide. Further, each of these compounds sulfamide and sulfoxamide continue to contain an active hydrogen atom when one or more of their nitrogen atoms are mono-substituted with a hydrocarbyl group, thus rendering them reactive with an acid halide and suitable for use in providing a precursor according to the invention. For convenience, the substituted and unsubstituted sulfamides and sulfoxamides used as an initial raw material in providing a composition or compound according to the invention may be collectively denoted as:

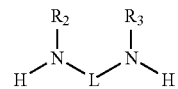

in which L is a divalent radical that is selected from the group consisting of:

and wherein $R_2$ and $R_3$ are each independently selected from the group consisting of: hydrogen and any $C_1$ to $C_{20}$ hydrocarbyl group.

Thus, the preparation of a precursor according to one preferred embodiment of the invention may be accomplished by conducting the reaction:

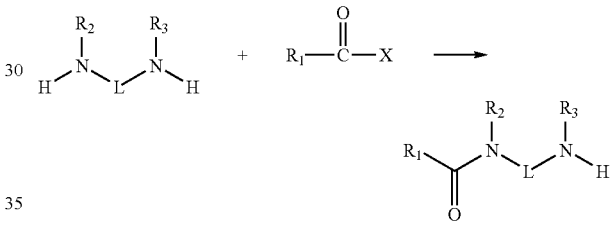

In this reaction, one mole of acid halide is shown to be reacted with each mole of substituted or unsubstituted sulfamide (or sulfoxamide when selected) reactant, and although not specifically written, in the process a mole of hydrogen halide HX is liberated. However, those of ordinary skill in the art readily appreciate that more than one mole of acid halide may be employed per mole of sulfamide (or sulfoxamide when selected). Particularly, when $R_2$ and $R_3$ are both hydrogen, it is possible to append up to four groups having structure:

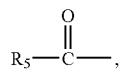

in which $R_5$ is independently hydrogen or any $C_1$ to $C_{20}$ hydrocarbyl group to the starting material:

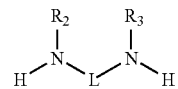

Thus, one embodiment of the invention provides a precursor which may be formed according to the reaction:

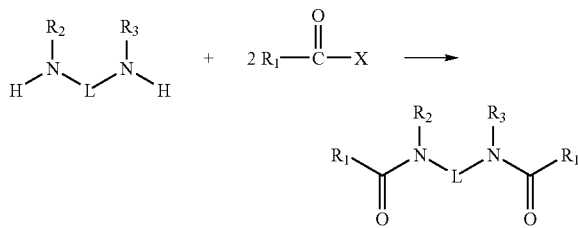

in which 2 moles of the same acid halide are reacted with each mole of sulfamide (or sulfoxamide, when selected), and in such a process two moles of hydrogen halide HX are liberated. In the above two reactions, the identities of the various substituents are as previously described, namely L is a divalent radical that may be either of

and $R_1$ may be any $C_1$ to $C_{20}$ hydrocarbyl group; and $R_2$ and $R_3$ are each independently selected from the group consisting of: hydrogen and any $C_1$ to $C_{20}$ hydrocarbyl group.

These reactions fall under the general reaction:

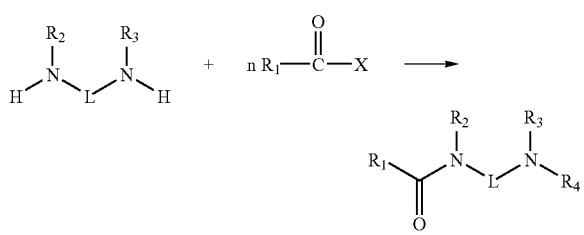

in which L is a divalent radical that may be either of

n preferably has the value of either one or two; $R_1$ may independently be any $C_1$ to $C_{20}$ hydrocarbyl group; $R_2$, and $R_3$ in the reactant may independently be hydrogen, or any $C_1$ to $C_{20}$ hydrocarbyl group, and $R_2$ and $R_3$ in the product are each independently hydrogen, any $C_1$ to $C_{20}$ hydrocarbyl group, or the group:

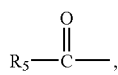

in which $R_5$ is independently hydrogen or any $C_1$ to $C_{20}$ hydrocarbyl group, and $R_4$ is hydrogen or the group:

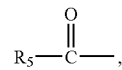

in which $R_5$ is independently hydrogen or any $C_1$ to $C_{20}$ hydrocarbyl group. Alternate preferred embodiments include the cases where n is selected to be 3 when at least one of $R_2$ and $R_3$ in the reactant are hydrogen, and where n is selected to be 4 when both of $R_2$ and $R_3$ in the reactant are hydrogen. The liberated HX is not specified in the general reaction but is recognized as being liberated by those skilled in the art, in a quantity that depends upon the total amount of acid halide and active hydrogen atoms present in the reactant sulfamide or sulfoxamide.

Thus, using a process as described above in combination with the specified starting materials, the invention provides compositions of matter useful for forming peroxygen acids, which comprise an amino compound having the structure:

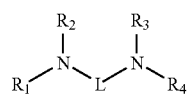

in which L is a divalent radical that is independently selected from the group consisting of:

and wherein $R_1$, $R_2$, $R_3$, and $R_4$ are each independently selected from the group consisting of: hydrogen, any $C_1$ to $C_{20}$ hydrocarbyl group, and the group:

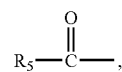

in which $R_5$ is in each occurrence independently hydrogen or any $C_1$ to $C_{20}$ hydrocarbyl group. In a preferred embodiment, at least one of $R_1$, $R_2$ $R_3$, and $R_4$ are the group:

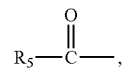

in which $R_5$ is in each occurrence independently hydrogen or any $C_1$ to $C_{20}$ hydrocarbyl group. In another preferred embodiment, at least one of $R_1$ and $R_2$ are the group:

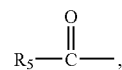

in which $R_5$ is in each occurrence independently hydrogen or any $C_1$ to $C_{20}$ hydrocarbyl group and at least one of $R_3$ and $R_4$ are the group:

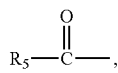

in which $R_5$ is in each occurrence independently hydrogen or any $C_1$ to $C_{20}$ hydrocarbyl group.

The processes in all of the these reactions set forth above are considered to be acylation reactions, and their reaction products are useful in preparing solutions containing peroxygen acids upon their being mixed with an aqueous peroxide such as hydrogen peroxide or a peroxide precursor, such as percarbonate or perborate anions, in aqueous media. The acylation reactions described above for preparing the precursors of the invention are preferably carried out in a solvent, which solvent is preferably an organic solvent in which the acid halide and sulfamide (or sulfoxamide, when employed) are mutually soluble. In addition, it is preferable to add a small amount of tertiary amine, such as a tri-alkyl amine such as triethylamine, trimethylamine, pyridine, etc. to the solution to facilitate the reaction between the acid halide and sulfamide (or sulfoxamide), as the use of tertiary amines for this purpose is known in the art.

It will be immediately recognized by those skilled in the art upon reading this specification that the identity of the hydrocarbyl groups $R_1$ and $R_5$ will often be the same, as in those cases when two moles of acid halide are combined with one mole of the sulfamide (or sulfoxamide when selected). However, it is possible for the identities of the hydrocarbyl groups $R_1$ and $R_5$ to be different from one another in a precursor product according to the invention, and such result is readily accomplished by first reacting a selected sulfamide (or sulfoxamide) having two active hydrogen atoms, either on the same nitrogen atom or on different nitrogen atoms, with a first acid halide, and then subsequently reacting the acylated product with a second acid halide having an R group that differs from that of the first acid halide. During the course of such reactions, owing to thermodynamic and kinetic equilibria, it is statistically probable that a portion of the reaction product will be one in which $R_2$ may comprise the group:

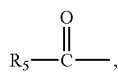

in which $R_5$ may comprise the same group as $R_1$, for the case when two moles of acid halide are reacted in a single reaction step with each sulfamide (or sulfoxamide) present, when the sulfamide (or sulfoxamide) initially comprises two active hydrogen atoms attached to the same nitrogen in the reactant (with $R_3$ and $R_4$ being as specified above) By the same token, in an alternate form of the invention $R_5$ in a radical:

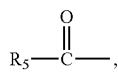

in the position of $R_2$ may comprise a different group than $R_1$, for the case when two moles of acid halide are reacted in two separate reaction steps with each sulfamide (or sulfoxamide) present, when the sulfamide (or sulfoxamide) initially comprises two active hydrogen atoms attached to the same nitrogen in the reactant. Thus, although the most kinetically favored reaction product is represented by:

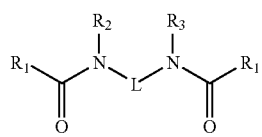

there will nevertheless also be present certain quantities of material represented by the structure:

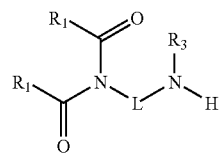

the relative amount of which depends on the nature of the $R_1$ group, as is readily appreciated by those skilled in the art, when the $R_2$ group in the reactant which results from the monoacylation of the sulfamide (or sulfoxamide) raw material:

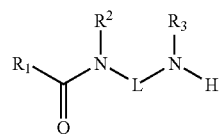

comprises hydrogen. Thus, the present invention also includes compositions having the general structure:

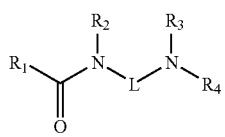

in which $R_2$ comprises the radical:

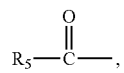

in which $R_5$ is independently hydrogen or any $C_1$ to $C_{20}$ hydrocarbyl group. However, the preferred inventive compounds are those described by the formula:

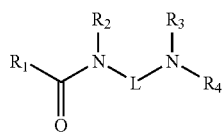

in which L is a divalent radical that is independently selected from the group consisting of:

and wherein $R_1$ is independently any $C_1$ to $C_{20}$ hydrocarbyl group; $R_2$ and $R_3$ are each independently selected from the group consisting of: hydrogen and any $C_1$ to $C_{20}$ hydrocarbyl group; and $R_4$ is independently selected from the group consisting of: hydrogen, and the group

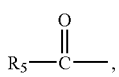

in which $R_5$ is independently hydrogen or any $C_1$ to $C_{20}$ hydrocarbyl group are water soluble at room temperature, are more efficient in generating peracids than currently-available commercial precursors, and these materials can be advantageously used as solid precursors to peroxy acids when mixed with hydrogen peroxide or a hydrogen peroxide precursor such as percarbonate or perborate.

The following preparatory methods are intended to be exemplary of the present invention and shall not be construed to be delimitive thereof in any respect.

EXAMPLE 1

Synthesis of diproprionyl sulfamide—To 100 ml of toluene in a flask equipped with a reflux condenser and a mechanical stirrer under moderate agitation are added 9.6 grams of sulfamide and 10.1 grams of triethylamine, and stirring is continued until complete dissolution occurs. Next, 9.25 grams of proprionyl chloride is added dropwise with stirring over the course of about 15 minutes, while the temperature of the flask is maintained below 60° C. After the addition of the proprionyl chloride is complete, the mixture is allowed to cool to room temperature, after which time it is filtered to remove the triethylamine hydrochloride by-product, which is discarded. The toluene is removed using a rotary evaporator until crystals just begin to form, at which time the flask contents are cooled to between about 2-8° C. overnight to complete crystallization process. The product is filtered, dried under vacuum, and stored in a dessicator. The overall reaction is:

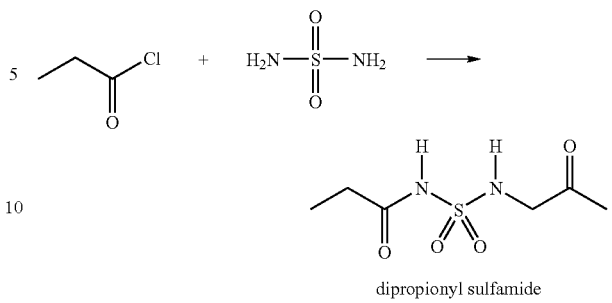

dipropionyl sulfamide

EXAMPLE 2

The procedure according to Example 1 is followed, except 13.0 grams of propionic anhydride is utilized in place of the proprionyl chloride.

EXAMPLE 3

Synthesis of dipropionyl sulfoxamide—To 100 ml of toluene in a round bottom flask equipped with a reflux condenser and a mechanical stirrer under moderate agitation are added 8.0 grams of sulfoxamide and 10.1 grams of triethylamine until dissolution is complete. Subsequently, 9.25 grams of proprionyl chloride is added dropwise with stirring by means of an addition funnel while taking care to maintain the mixture below 60° C. Following the addition the mixture is allowed to cool to room temperature, and is filtered to remove triethylamine hydrochloride by-product, which is discarded. The toluene is evaporated using a rotary evaporator until crystals just begin to form, after which time the contents of the flask are cooled to between 2-8° C. and allowed to stand overnight to complete crystallization process. The product is filtered, dried under a vacuum, and stored in a dessicator the overall reaction is:

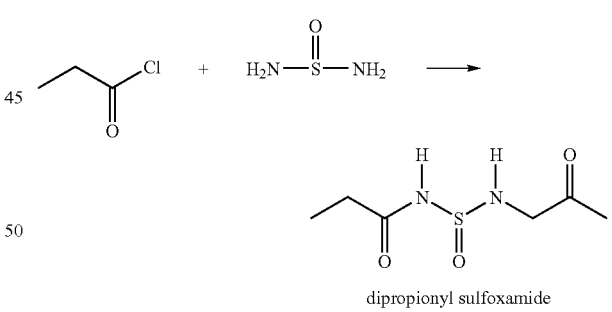

dipropionyl sulfoxamide

EXAMPLE 4

The procedure according to Example 3 is followed, except that 13.0 grams of propionic anhydride is utilized in place of the proprionyl chloride.

PRACTICAL USE EXAMPLE

An equimolar amount of sodium perborate and diproprionyl sulfamide are mixed with water sufficient to generate ~0.4% perpropionic acid. To make one liter of product mix 4.8 grams of diproprionyl sulfamide with 4.65 grams of sodium perborate and add one liter of water. The reaction mixture will be initially basic, then as the reaction proceeds the pH will drop. Sufficient buffer such as sodium dihydrogen phosphate should be added such that the final pH is between ~6.5 and ~7.0. To enhance microbial activity, ionic or nonionic surfactants such as dodecylbenzenesulfonic acid or pluronics may be added. Sequestering agents such as ethylenediaminetetraacetic (FDTA) acid may be added to improve microbial activity.

For the sake of stability of an aqueous solution containing an amino compound according to the invention, it is preferred that the aqueous solution contain a pH buffer. The buffer chosen is not critical as long as the proper pH is maintained preferably in the range of between about 5.0 to 7.0. A vast number of buffers are known to those skilled in the art, and any buffer known to those skilled in the art as being useful for maintaining an aqueous solution that contains an amino compound according to the invention in the range specified above may be used for this purpose, with the main proviso for suitability being that the components of such buffer are preferably stable with respect to the other chemical species in the aqueous solution. Suitable buffer systems thus include without limitation: phosphate buffers; sulfate buffers; acetic/acetate buffers; propionic/proprionate buffers; $C_1$-$C_{10}$ mono- and polycarboxylic acid buffers; substituted carboxylic acids such as lactic, ascorbic, and tartaric acid buffers; and carboxylic acids that have unsaturation such as maleic and furmaric buffers. Buffer systems are known to contain salt pairs. Currently, the most preferred buffer is the dihydrogen phosphate buffer, adjusted to a pH of about 6.5.

Sequesterants may be used to advantage as a component of an aqueous solution that contains an amino compound according to the invention, for tying up or otherwise rendering chemically unavailable various species which may otherwise tend to interfere with the performance of the compounds and/or solutions of the invention. Suitable sequesterants include those commonly employed in the surfactant and other industries, including without limitation EDTA or analogous phosphonic acid salts, tartarates, citrates, and other species recognized by those skilled in the art as capable of functioning as a sequesterant.

Other soluble conventional materials may be present to advantage as a component of an aqueous solution that contains an amino compound according to the invention, including corrosion inhibitors, dyes, perfumes, germicides, preservatives, e.g., quaternium 15, anti-tarnishing agents, surfactants (for example anionic, cationic, nonionic, amphoteric or mixtures thereof), thickeners, chelating agents, antioxidants, and the like. Such other conventional materials may be used in the amounts they are normally used generally up to about 5% by weight, more preferably up to about 3% by weight.

The invention also provides a process for disinfecting various microbes, including bacteria, molds, fungi and their spores which comprises contacting the vapor of peroxy acid generated as described herein in conjunction with a conventional means of vaporization selected from the group consisting of: heat, venturi nebulization, and sonication with at least one of said microbes.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. The present invention further includes all possible combinations of the features recited in the specification and/or any one of the various claims appended hereto with the features recited elsewhere in the specification and/or in any one or more of each of the remaining claims. For example, the present specification includes disclosure of a process according to claim 18 which comprises contacting a composition according to any of claims 1-17 with an aqueous peroxide. Accordingly, the presently disclosed invention is intended to cover all such modifications, alterations, and combinations.

What is claimed is:

1. A composition of matter useful for forming organic peroxy acids, which comprises a polyamino compound having the structure:

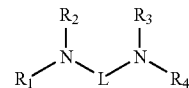

in which L is a divalent radical that is independently selected from the group consisting of:

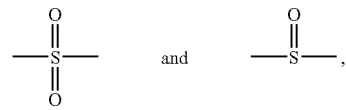

and wherein $R_1$, $R_3$, $R_4$ are each independently selected from the group consisting of: hydrogen, any $C_1$ to $C_{20}$ hydrocarbyl group, and the group:

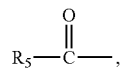

wherein both of the nitrogen atoms in said structure do not have the same substituents appended thereto; and wherein both of the substituents in a pair selected from the group consisting of: $R_1$ and $R_2$; and $R_3$ and $R_4$ are the group:

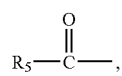

in which $R_5$ is independently in each occurrence hydrogen or any $C_1$ to $C_{20}$ hydrocarbyl group; and wherein at least one of the groups of $R_1$, $R_2$, $R_3$, and $R_4$ which are not the group:

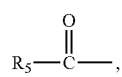

is hydrogen.

2. A composition of matter useful for forming organic peroxy acids, which comprises a polyamino compound having the structure:

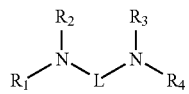

in which L is a divalent radical that is independently selected from the group consisting of:

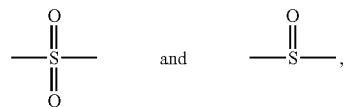

and wherein $R_1$, $R^2$, $R_3$, $R_4$ are each independently selected from the group consisting of: hydrogen, any $C_1$ to $C_{20}$ hydrocarbyl group, and the group:

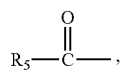

subject to the provisos that: both of the nitrogen atoms in said structure do not have the same substituents appended thereto; and wherein any three of $R_1$, $R_2$, $R_3$, and $R_4$ are the group:

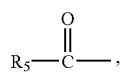

in which $R_5$ is independently in each occurrence hydrogen or any $C_1$ to $C_{20}$ hydrocarbyl group.

3. A composition according to claim 2 wherein the group of $R_1$, $R_2$, $R_3$, and $R_4$ which is not a group:

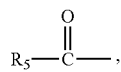

is hydrogen.

4. A composition according to claim 2 wherein the group of $R_1$, $R_2$, $R_3$, and $R_4$ which is not a group:

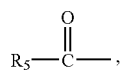

is any $C_1$ to $C_{20}$ hydrocarbyl group.

5. A composition of matter useful for forming organic peroxy acids, which comprises a polyamino compound having the structure:

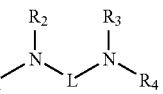

in which L is a divalent radical that is independently selected from the group consisting of:

wherein all of $R_1$, $R_2$, $R_3$, and $R_4$ are the group:

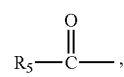

in which $R_5$ is independently in each occurrence hydrogen or any $C_1$ to $C_{20}$ hydrocarbyl group.

6. A composition of matter useful for forming organic peroxy acids, which comprises a polyamino compound having the structure:

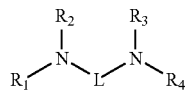

in which L is a divalent radical that is independently selected from the group consisting of:

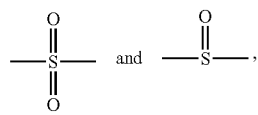

wherein $R_1$ and $R_4$ are represented by the group:

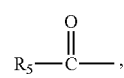

in which $R_5$ is independently in each occurrence hydrogen or any $C_1$ to $C_{20}$ hydrocarbyl group, and wherein $R_2$ and $R_3$ are each hydrogen.

7. A composition according to claim 6 wherein $R_5$ in each occurrence is independently selected from the group consisting of: hydrogen, a methyl, an ethyl, a propyl, and a butyl group.

* * * * *

UNITED STATES PATENT AND TRADEMARK OFFICE
CERTIFICATE OF CORRECTION

PATENT NO. : 7,307,191 B2
APPLICATION NO. : 10/800788
DATED : December 11, 2007
INVENTOR(S) : David W. Hobson and Danny O. Helton It is certified that error appears in the above-identified patent and that said Letters Patent is hereby corrected as shown below:

Title Page;

"(75) Inventors: David W. Hobson, San Antonio, TX (US); Danny O. Helton, Newberry, FL (US)"

should read

-- (75) Inventors: Danny O. Helton, Newbury, FL (US); David W. Hobson, Boerne, TX (US); --

Title Page;

"(73) Assignee: OH Technologies LLP, Boerne, TX (US)"

should read

-- (73) Assignee: DH TECHNOLOGIES, LLP, Boerne, TX (US) --

Signed and Sealed this

Fifteenth Day of April, 2008

JON W. DUDAS
*Director of the United States Patent and Trademark Office*